US006623272B2

(12) United States Patent
Clemans

(10) Patent No.: US 6,623,272 B2
(45) Date of Patent: Sep. 23, 2003

(54) LIGHT-EMITTING TOOTHBRUSH AND METHOD OF WHITENING TEETH

(76) Inventor: Kathleen Clemans, 13642 Sunset Blvd., Pacific Palisades, CA (US) 90272

( * ) Notice: Subject to any disclaimer, the term of this patent is extended or adjusted under 35 U.S.C. 154(b) by 0 days.

(21) Appl. No.: 10/008,762

(22) Filed: Nov. 30, 2001

(65) Prior Publication Data

US 2003/0104340 A1 Jun. 5, 2003

(51) Int. Cl.[7] ................................................. A61C 5/00
(52) U.S. Cl. ...................................... 433/215; 433/216
(58) Field of Search ........................... 433/29, 215, 216

(56) References Cited

U.S. PATENT DOCUMENTS

| | | | |
|---|---|---|---|
| 4,253,212 A | 3/1981 | Fujita | 15/167 R |
| 4,779,173 A | 10/1988 | Carr et al. | 362/109 |
| 4,788,734 A | 12/1988 | Bauer | 15/105 |
| 5,030,090 A | 7/1991 | Maeda et al. | 433/29 |
| 5,160,194 A | 11/1992 | Feldman | 362/109 |
| 5,658,148 A | 8/1997 | Neuberger et al. | 433/215 |
| 5,698,182 A | 12/1997 | Prencipe et al. | 424/53 |
| 5,713,738 A | 2/1998 | Yarborough | 433/215 |
| 5,785,957 A | 7/1998 | Losee et al. | 424/53 |
| 5,800,165 A | 9/1998 | Kirsch et al. | 433/29 |
| 5,824,291 A | 10/1998 | Howard | 424/48 |
| 5,879,691 A | 3/1999 | Sagel et al. | 429/401 |
| 5,885,273 A * | 3/1999 | Eckhouse et al. | 606/9 |
| 5,894,620 A * | 4/1999 | Polaert | 15/22.1 |
| 5,922,307 A | 7/1999 | Montgomery | 424/53 |
| 5,972,374 A | 10/1999 | Theisen | 424/440 |
| 5,989,569 A | 11/1999 | Dirksing et al. | 424/401 |
| 6,026,828 A * | 2/2000 | Altshuler | 132/311 |
| 6,029,304 A | 2/2000 | Hulke et al. | 15/105 |
| 6,036,493 A | 3/2000 | Sharma | 433/216 |
| 6,056,548 A | 5/2000 | Neuberger et al. | 433/215 |
| 6,094,767 A * | 8/2000 | Iimura | 15/105 |
| 6,106,293 A | 8/2000 | Wiesel | 433/215 |
| 6,106,294 A | 8/2000 | Daniel | 433/216 |
| 6,108,850 A | 8/2000 | McLaughlin | 15/167.1 |
| 6,149,895 A | 11/2000 | Kutsch | 424/53 |
| 6,154,912 A | 12/2000 | Li | 15/105 |
| 6,155,832 A | 12/2000 | Wiesel | 433/215 |
| 6,162,055 A | 12/2000 | Montgomery et al. | 433/216 |
| 6,202,242 B1 | 3/2001 | Salmon et al. | 15/22.1 |
| 6,221,341 B1 | 4/2001 | Montgomery | 424/53 |
| 6,290,496 B1 * | 9/2001 | Azar et al. | 433/29 |

* cited by examiner

*Primary Examiner*—Cary E. O'Connor
(74) *Attorney, Agent, or Firm*—Fulbright & Jaworski L.L.P.

(57) ABSTRACT

A light-emitting toothbrush comprising a head having a plurality of bristles affixed to and extending from a first side, a handle detachably affixed to a second side of the head, a light guide having a first end disposed within the head and a second end disposed within the handle, and a light source optically coupled to the second end of the light guide. The light source emits light having a spectrum ranging from about 350 nanometers to about 700 nanometers. Light from the light source entering the light guide is guided to the first end of the light guide and out of the first side of the head. Thus the light emitted from the head illuminates teeth while brushing.

16 Claims, 1 Drawing Sheet

LIGHT-EMITTING TOOTHBRUSH AND METHOD OF WHITENING TEETH

BACKGROUND OF THE INVENTION

1. Field of the Invention

The field of the present invention is dental cosmetics, and more specifically the cosmetic whitening of teeth through photochemical processes.

2. Background

Teeth whitening processes have quickly become some of the most sought after cosmetic dental procedures by many individuals. The popularity appears to stem from the self esteem people obtain from having classic, pearly white teeth which are free from stains that result from drinking beverages such as coffee or tea, eating foods containing dyes, or smoking.

Teeth whitening procedures may be performed at a dental office or in the comfort of one's own home. The in-office procedures usually achieve better results, in a much shorter amount of time, than at home procedures. However, the in-office procedures are often expensive and lengthy, as they may cost approximately $500 or more and may require the patient to sit in the dentist's chair for over an hour with an open mouth while the procedure is performed. One example of an in-office procedure is disclosed in U.S. Pat. No. 5,713,738. In that procedure, the patient's mouth is first prepared so that only the teeth are exposed and the gums are protected. Then, an oxidizing bleaching solution is applied to the teeth and the teeth are exposed one at a time to light from an argon laser. Further bleaching is possible by applying a second bleaching solution and exposing the teeth to light from a carbon dioxide laser. This entire process can be time consuming, and therefore expensive.

A second in-office procedure is disclosed in U.S. Pat. No. 6,162,055. For this procedure, a photosensitizing agent is first applied to the teeth followed by an oxidizing bleaching solution. The teeth are then exposed to light in the visible spectrum to activate the photosensitizer and the bleaching solution, thus accelerating the bleaching process. The light of this procedure is limited to visible light because of the potential harmful effects of UV and infrared radiation to the teeth and gums. This procedure tends to take less time than the procedure described in the '738 patent. However, as with any visit to the dental office, it may be a costly cosmetic procedure. Thus, for many individuals, the requirements of in-office teeth whitening procedures present too great of an inconvenience, leaving a desire for alternative teeth whitening processes.

Home teeth whitening procedures may be favored over the in-office procedures because they enable teeth whitening in the comfort and convenience of one's own home. However, the currently available home products have their own limitations. Teeth whitening at home may be performed through the use of whitening tooth pastes. However, whitening toothpastes often yield unsatisfying results because they are often not effective on harsh stains and they must be used for extended periods of time to achieve noticeable results.

Other at home processes have thus been developed in an attempt to increase the whitening obtainable through home processes and decrease the time it takes to achieve noticeable results. These more recent processes frequently require a tray, the tray being either a generic tray, such as the one described in U.S. Pat. No. 6,089,869, or a plastic strip, such as the one described in U.S. Pat. No. 5,879,691, to be placed in the mouth for an hour or more at a time. The tray or plastic strip includes a bleaching solution, and while the tray is worn, the teeth are slowly whitened. The whitening process typically takes a period of weeks.

One drawback of these home teeth whitening devices is that they may interfere with normal daily activity if worn during the daytime. Therefore, the devices are frequently worn only at night while sleeping. However, for some even having to wear such devices at night presents an inconvenience. An additional drawback of these home devices is that the whitening achieved tends to be less significant than the in-office procedures.

SUMMARY OF THE INVENTION

The present invention is directed to a light-emitting toothbrush and a method of whitening teeth. The toothbrush comprises a head having bristles affixed to a first side, a handle affixed to a second side of the head, a light source, and a light guide having a first end disposed within the head and a second end optically coupled to the light source. The light source emits light in a spectrum ranging from about 350 nanometers to about 700 nanometers, although narrower spectra may also be used. The light guide is formed and positioned so that light entering the second end of the light guide is guided to the first end and directed out of the first side of the head. Thus, when teeth are brushed using the toothbrush, light emitted from the head is directed towards the teeth.

The light source may be disposed within the handle or external to the handle. For an external light source, the light source may be optically coupled to the waveguide using an optical fiber. A band pass filter may be included with the light source so that only light within the desired spectrum passes into the waveguide.

The method of the present invention is directed to a process for whitening teeth. A bleaching solution is first applied to the teeth or to the bristles of a toothbrush, followed by generating light in a spectrum ranging from about 350 nm to about 700 nm. The generated light is guided out of the side of the toothbrush to which the bristles are affixed. Teeth may then be brushed to gain the benefits of photo-bleaching to whitening the teeth. The bleaching solution includes an oxidizer selected from the group consisting of carbamide peroxide, carbamyl peroxide, sodium percarbonate, perhydrol urea, peroxyacetic acid, and hydrogen peroxide.

Accordingly, it is an object of the present invention to provide a light-emitting toothbrush and a method of whitening teeth. Other objects and advantages will appear hereinafter.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
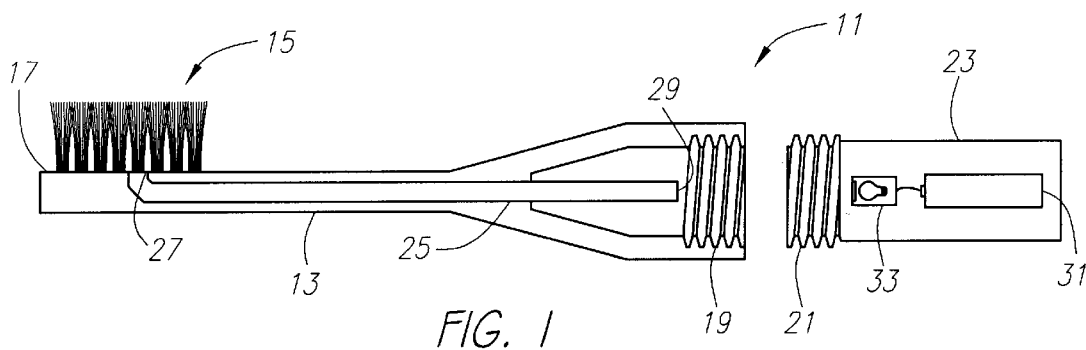
FIG. 1 illustrates a side sectional view of toothbrush according to a preferred embodiment of the present invention.

Turning in detail to the drawings, FIG. 1 illustrates a light-emitting electric toothbrush 11 in accordance with a preferred embodiment of the present invention. The electric toothbrush 11 comprises a head 13 having a plurality of bristles 15 affixed to and extending from a first side 17. The head 13 includes an interiorly threaded portion 19 which mates to an exteriorly threaded portion 21 on the handle 23. The head 13 is thus detachably affixed the handle 23, allowing multiple heads to be utilized with a single handle. A light guide 25 is disposed within the head 13 such that a first end 27 of the light guide 25 terminates at the first side 17 of the head 13 and such that the second end 29 of the light guide 25 is optically coupled to the light source 33 when the head 13 is affixed to the handle 23. The shape of light guide 25 is such that light entering the second end 29 is guided towards the first end 27 and directed out of the first side 17 of the head 13. By shaping the light guide 25 in this manner, teeth are illuminated during brushing. The illumination helps accelerate the photo-bleaching process of whitening teeth, a process that is well known to those skilled in the art.

A power source 31, preferably a rechargeable battery, a light source 33, and a drive mechanism (not shown) are disposed within the handle 23 of the electric toothbrush 11. The power source 31 is coupled to and provides power to both the light source 33 and the drive mechanism. The drive mechanism provides the mechanical motion that moves the bristles 15 appropriately to assist in cleaning teeth. The motion of the bristles may be circulatory, vibratory, or any other type of motion which is appropriate for providing mechanical assistance in cleaning teeth. Drive mechanisms for electric toothbrushes are well known to those skilled in the art and as such are not discussed in detail herein.

The light guide 25 may be formed of any material that is transparent to light in the visible spectrum. In addition, more than a single light guide may be used. For example, two or more light guides may direct light from the light source to the head along adjacent paths. At the head, the light guides may diverge so that light is directed out of the head at multiple locations on the first side. Alternatively, one or more light guides may direct the light into the bristles if the bristles are formed of light transmitting material, such as is described in U.S. Pat. No. 5,030,090 and U.S. Pat. No. 6,056,548, the disclosures of which are incorporated herein by reference. In such an embodiment, the light will pass out of the head of the toothbrush through the bristles and be directed towards the surface of teeth during brushing.

The light source 33 includes a lamp 35 and a band pass filter 37. Light emitted from the light source 33 has a spectrum ranging from about 350 nm to about 700 nm, and preferably ranging from about 350 nm to about 500 nm. The lamp 35 may be any type of lamp that emits light in the desired spectrum. For lamps that emit wavelengths outside of the desired spectrum, the band pass filter 37 limits the emitted light to wavelengths within the desired spectrum. The band pass filter 37 may comprise a dichroic filter or any other type of wavelength selection device known to those skilled in the art.

The emitted light may include light outside the desired spectrum where such light is a necessary artifact of the light generating and filtering processes. For example, a band pass filter designed to pass light between 350 nm and 700 nm may leak low levels of light in the 325 nm to 349 nm range and/or the 701 nm to 725 nm range. Such leakage, provided it is remains at low levels, is considered within the spectral range of the present invention, as it often cannot be avoided.

Figure 4:
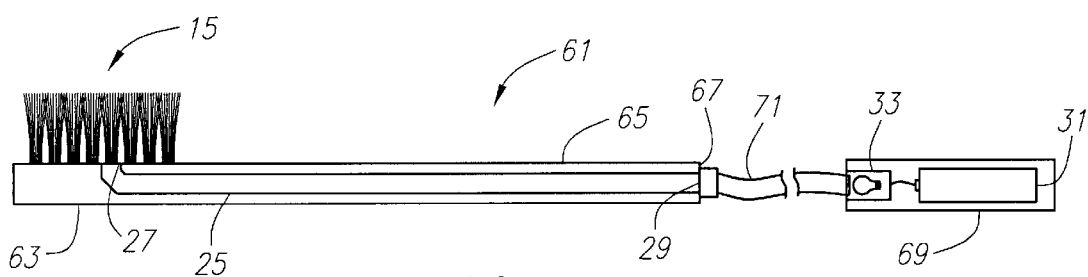
FIG. 4 illustrates a side sectional view of a toothbrush according to a second alternative embodiment of the present invention.

The spectrum of light emitted from the light source is limited to the indicated ranges to eliminate potentially harmful wavelengths in the near-infrared, the infrared, and the UV spectra. Prolonged or repeated exposure to light in these spectra may cause damage to teeth and/or gums. Lamps which produce light in the desired spectrum and which may disposed in the handle include tungsten halogen lamps, incandescent lamps, or krypton lamps, among others. As is further discussed below, alternative lamps and light sources may be utilized if the lamp or light source is disposed externally to the toothbrush, such as is illustrated in FIG. 4. These alternative lamps or light sources are preferably disposed externally to the toothbrush because of the high amounts of heat they tend to generate or because of their bulk.

Figure 2A:
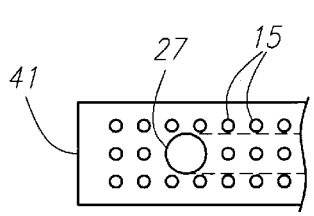
FIGS. 2A & 2B illustrate close-up top views of head configurations for the toothbrush of FIG. 1.
Figure 2B:
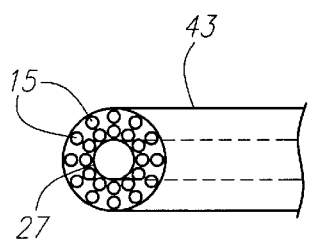

FIGS. 2A and 2B illustrate examples of bristle configurations on the head of a toothbrush. Other bristle configurations are also contemplated. The bristles 15 may be of the type which are commonly used for toothbrushes. FIG. 2A illustrates a common rectangular bristle configuration. With this configuration, the first end 27 of the light guide 25 is preferably positioned approximately in the center of the head 41 for efficient illumination of teeth during brushing. FIG. 2b illustrates a common circular bristle formation, such as is found on some rotary electric toothbrushes. Again, the first end 27 of the light guide 25 is preferably positioned approximately in the center of the head 43. The actual positioning of the bristles 15 may vary. However, regardless of the actual bristle configuration, the bristles 15 are preferably positioned so that they do not significantly interfere with light emerging from the light guide 25, as interference tends to reduce the effectiveness of the whitening process.

Figure 3:
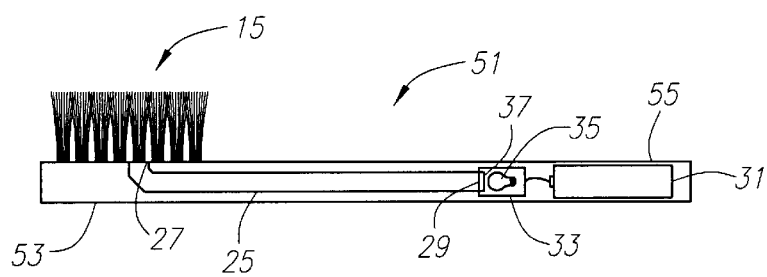
FIG. 3 illustrates a side sectional view of a toothbrush according to a first alternative embodiment of the present invention.

FIGS. 3 and 4 illustrate alternative embodiments of the present invention. In FIG. 3, a light-emitting manual toothbrush 51 comprises a head portion 53 integrated with a handle portion 55. The light source 33 and power source 31 are disposed within the handle portion 55, and the light guide 25 has a first end 27 disposed within the head 53 portion and a second end 29 disposed within the handle portion 55 and optically coupled to the light source 33.

In FIG. 4, the light-emitting manual toothbrush 61 comprises a head portion 63 integrated with a handle portion 65. The light guide 25 is disposed within the toothbrush 61 with the second end 29 of the light guide 25 terminating at the end 67 of the handle portion 65. The light source 33 and power source 31 are integrated into an external unit 69 that is disposed externally to the toothbrush 61, and the light source 33 is optically coupled to the second end 29 of the light guide 25 by an optical fiber 71. The optical fiber is preferably flexible enough so as not to inhibit the teeth brushing process. Such an optical fiber 71 may be of any type that is transparent to light in the visible spectrum.

An advantage obtained by the embodiment of FIG. 4 is that the light source 33 may comprise a high intensity lamp or other more bulky light source such as some lasers. High intensity lamps may not be appropriate for placement in the handle because of the risk of burn to the user due to the heat generated. Therefore, such lamps are preferably placed externally to the handle. Lamps such as metal halide lamps, linear flash lamps, short arc lamps using Xenon, Mercury, Argon, or a combination thereof, or any other type of high intensity lamp may be used. Lasers emitting light in the desired spectrum are preferably used externally as such lasers tend to be too bulky to be disposed within the handle. In addition, many high intensity lamps and lasers often require necessarily large power supplies that are too large to be disposed within the handle of a toothbrush.

The method of whitening teeth utilizes a light-emitting toothbrush to whiten teeth by taking advantage of photo-bleaching effects. A bleaching solution, the solution being preferably a liquid or a gel, is applied to the surface of teeth or to the bristles of a light-emitting toothbrush. When used at home, the bleaching solution may be a over-the-counter solution comprised of 5% hydrogen peroxide. The bleaching solution may also comprise a more concentrated hydrogen peroxide solution, but such solutions typically need to be prescribed by a dentist. The bleaching solution may also contain an oxidizer selected from the group consisting of the following oxidizers: carbamide peroxide, carbamyl peroxide, sodium percarbonate, perhydrol urea, and peroxy-acetic acid. The actual concentration of the oxidixer determines how quickly the whitening process proceeds. It may also be desirable to include a photosensitizer in the bleaching solution to further enhance the whitening process. One example of such a solution is disclosed in U.S. Pat. No. 6,162,055, the disclosure of which is incorporated herein by reference.

After applying the bleaching solution to the teeth, light having a spectral range as previously described herein is generated. In the preferred embodiment the light is generated from a light source disposed within the toothbrush, or alternatively, the light may be generated from a light source disposed externally to the toothbrush. Where the light is generated from a source disposed within the toothbrush, the generated light is guided directly out of the side of the head to which the bristles are affixed. Where the light is generated from a source disposed externally to the toothbrush, the light is optically coupled to the toothbrush and then guided out of the side of the head to which the bristles are affixed. The generated light is guided out of the head so that when the bristles are used to brush teeth, the generated light illuminates the teeth. Any of the aforementioned light sources may be used to generate the light. Thus, when teeth are brushed using this method, the photo-bleaching effect enhances oxidation of the bleaching solution and accelerates the teeth whitening process.

Thus, a light-emitting toothbrush and a method of whitening teeth are disclosed. While embodiments of this invention have been shown and described, it would be apparent to those skilled in the art that many more modifications are possible without departing from the inventive concepts herein. The invention, therefore, is not to be restricted except in the spirit of the following claims.

What is claimed is:

1. A toothbrush comprising:
    a head having a plurality of bristles affixed to and extending from a first side of the head;
    a handle detachably affixed to a second side of the head;
    a light source which emits light in a spectrum ranging from at least 350 nanometers to at least 700 nanometers;
    at least one band pass filter optically coupled to the light source and adapted to pass light at wavelengths between about 350 nanometers and about 700 nanometers: and
    a light guide having a first end disposed within the head and a second end optically coupled to the at least one band pass filter, wherein light entering the second end of the light guide is guided towards the first end and directed out of the first side of the head.

2. The toothbrush of claim 1, wherein the light source is disposed within the handle.

3. The toothbrush of claim 1, wherein the light source is optically coupled to the light guide through an optical fiber.

4. The toothbrush of claim 1, wherein the at least one band pass filter is adapted to pass light at wavelengths between about 350 nanometers and about 500 nanometers.

5. The toothbrush of claim 1, wherein the first end of the light guide is optically coupled to the plurality of bristles such that light is guided out of the head through the bristles.

6. A toothbrush comprising:
    a body having a head portion and a handle portion;
    a plurality of bristles affixed to and extending from a first side of the head portion;
    a light source which emits light in a spectrum ranging from at least 350 nanometers to at least 700 nanometers;
    at least one band pass filter optically coupled to the light source and adapted to pass light at wavelengths between about 350 nanometers and about 700 nanometers; and
    a light guide having a first end disposed within the head portion and a second end optically coupled to the at least one band pass filter, wherein light entering the second end of the light guide is guided towards the first end and directed out of the first side of the head.

7. The toothbrush of claim 6, wherein the light source is disposed within the handle.

8. The toothbrush of claim 6, wherein the light source is optically coupled to the light guide through an optical fiber.

9. The toothbrush of claim 6, wherein the at least one band pass filter is adapted to pass light at wavelengths between about 350 nanometers and about 500 nanometers.

10. The toothbrush of claim 6, wherein the first end of the light guide is optically coupled to the plurality of bristles such that light is guided out of the head through the bristles.

11. A method of whitening teeth comprising:
    applying a bleaching solution to the teeth or to a plurality of bristles affixed to a first side of a toothbrush, the bleaching solution including an oxidizer;
    generating light having a spectrum ranging from about 350 nm to about 700 nm;
    guiding the generated light out of the first side of the toothbrush; and
    brushing the teeth with the toothbrush.

12. The method of claim 11, wherein generating light includes generating light from a light source disposed within the toothbrush.

13. The method of claim 11, wherein generating light includes generating light from a light source disposed externally to the toothbrush and optically coupling the light source to the toothbrush.

14. The method of claim 11, wherein generating light includes filtering light with a band pass filter to pass a spectrum ranging from about 350 nm to about 500 nm.

15. The method of claim 11, wherein guiding the generated light out of the first side of the toothbrush includes guiding the light through the plurality of bristles.

16. The method of claim 11, wherein the oxidizer is selected from the group consisting of carbamide peroxide, carbamyl peroxide, sodium percarbonate, perhydrol urea, peroxyacetic acid, and hydrogen peroxide.

* * * * *